(12) United States Patent
Hepper et al.

(10) Patent No.: US 8,697,067 B2
(45) Date of Patent: Apr. 15, 2014

(54) METHODS FOR INCREASING THE EFFECTIVENESS OF ANTIBODIES AND/OR FCY RECEPTOR-BINDING ACTIVE INGREDIENTS

(75) Inventors: Martin Hepper, Neustadt (DE); Hans Peter Leinenbach, Tholey (DE); Frank Nocken, Frankfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 239 days.

(21) Appl. No.: 12/440,319

(22) PCT Filed: Sep. 7, 2007

(86) PCT No.: PCT/EP2007/007840
§ 371 (c)(1),
(2), (4) Date: Jul. 17, 2009

(87) PCT Pub. No.: WO2008/028680
PCT Pub. Date: Mar. 13, 2008

(65) Prior Publication Data
US 2010/0166742 A1    Jul. 1, 2010

(30) Foreign Application Priority Data
Sep. 7, 2006   (DE) .......................... 10 2006 042 012

(51) Int. Cl.
*A61K 39/395*   (2006.01)
*G01N 33/53*    (2006.01)
*C07K 16/00*    (2006.01)

(52) U.S. Cl.
USPC ...................... 424/130.1; 435/7.1; 530/387.1

(58) Field of Classification Search
None
See application file for complete search history.

(56) References Cited

U.S. PATENT DOCUMENTS

| | | | |
|---|---|---|---|
| 4,681,870 A | | 7/1987 | Balint, Jr. et al. |
| 6,406,861 B1 * | | 6/2002 | Henderson et al. ............ 435/7.1 |
| 7,364,727 B2 * | | 4/2008 | Li et al. ........................ 424/93.2 |
| 7,691,587 B2 * | | 4/2010 | Atassi ............................ 435/7.1 |
| 2003/0125657 A1 * | | 7/2003 | Koll et al. ..................... 604/5.01 |

FOREIGN PATENT DOCUMENTS

EP    082 345    6/1983

OTHER PUBLICATIONS

Morgan et al. ( Neurochemistry, 2006, v.49, 190-194).*
Shimanovich et al., Clin.Exp.Dermatol., 2006, v.31, pp. 768-774).*
Borberg, Helmut et al, Quo Vadis Haemapheresis, Transfusion and Apheresis Science, Feb. 2006, pp. 51-73, vol. 34, No. 1, Elsevier Science, London, GB.
Kiewe Philipp, et al., Phase I Trial of the Trifunctional Anti-HER2 X Anti-CD3 Antibody Ertumaxomab in Metastatic Breast Cancer, Clinical Cancer Res., AACR Journals, May 15, 2006, pp. 3085-3091, vol. 12, No. 10.
Taylor, Ronald P. et al., Drug Insight: The Mechanism of Action of Rituximab in Autoimmune Disease—The Immune Complex Decoy Hypothesis, Nature Clinical Practice, Rheumatology, Feb. 2007, pp. 86-95, vol. 3, No. 2.
Preithner, Susanne, et al., High Concentrations of Therapeutic IgG1 Antibodies Are Needed to Compensate for Inhibition of Antibody-Dependent Cellular Cytotoxicity by Excess Endogenous Imunoglobulin G, Molecular Immunology 43, Elsevier Science, London, GB, pp. 1183-1193, 2001.
Montgomery, R A. et al., Plasmapheresis and Intravenous Immune Globulin Provides Effective Rescue Therapy for Refractory Humoral Rejection and Allows Kidneys to Be Successfully Transplanted Into Cross-Match-Positive Recipients, Transplantation, Sep. 27, 2000, pp. 887-895; vol. 70, No. 6, Lippincott et al., Baltimore, MD.
International Search Report, dated Nov. 13, 2007.
Jeffrey L. Browning—"B cells move to centre stage: novel opportunities for autoimmune disease treatment", Reviews, Jul. 2006, vol. 5, pp. 564-576.
Rech et al. "Immunoadsorption and CD20 antibody treatment in a patient with treatment resistant systemic lupus erythematosus and preterminal renal insufficiency." Ann Rheum Dis. Apr. 2006;65(4):552-3.
Rech et al. "Combination of immunoadsorption and CD20 antibody therapy in a patient with mixed connective tissue disease." Rheumatology (Oxford). Apr. 2006;45(4):490-1.
Tyden et al. "ABO incompatible kidney transplantations without splenectomy, using antigen-specific immunoadsorption and rituximab." Am J Transplant. Jan. 2005;5(1):145-8.

* cited by examiner

*Primary Examiner* — Michail Belyavskyi
(74) *Attorney, Agent, or Firm* — Millen, White, Zelano & Branigan, P.C.

(57) ABSTRACT

The present invention relates to an ex vivo method for increasing the effectiveness of antibodies and Fcγ receptor-binding active ingredients, comprising the steps of: a) preparing a blood sample of a patient; b) subjecting the blood sample to an immunoapheresis; c) administering a therapeutically effective antibody or an Fcγ receptor-binding active ingredient to the patient.

17 Claims, 1 Drawing Sheet

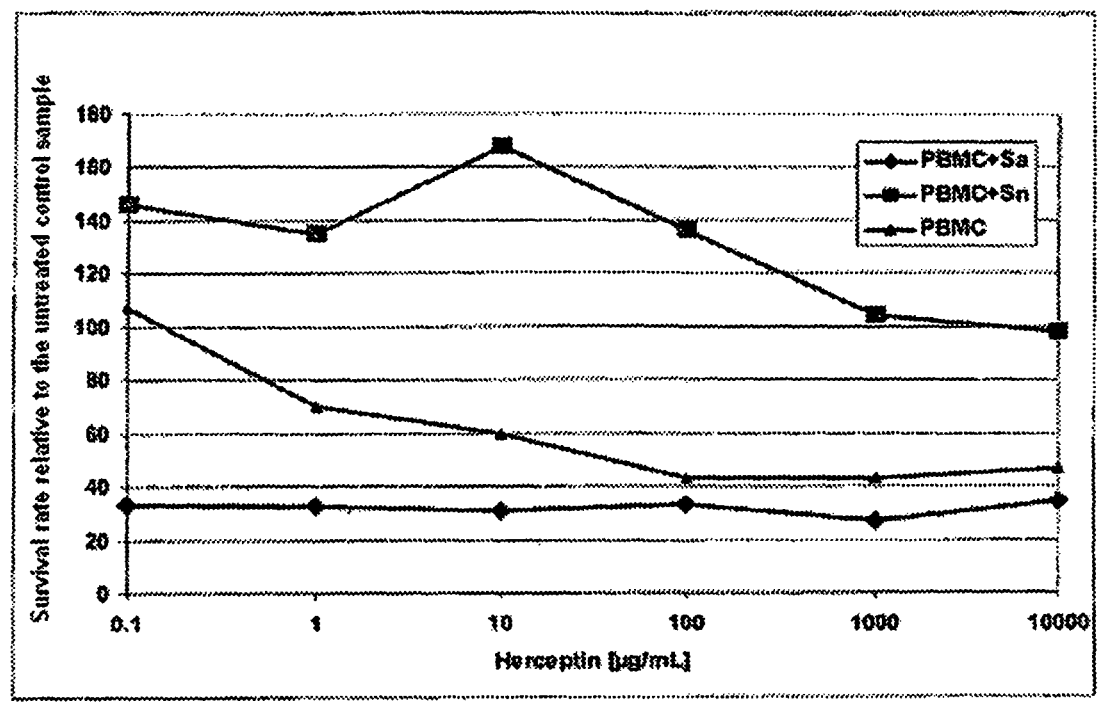

METHODS FOR INCREASING THE EFFECTIVENESS OF ANTIBODIES AND/OR FCγ RECEPTOR-BINDING ACTIVE INGREDIENTS

This is a U.S. National Phase application of application number PCT/EP2007/007840, filed Sep. 7, 2007 (which is incorporated herein by reference in its entirety), which claims priority benefit of DE 10 2006 042 012.8 filed Sep. 7, 2006.

FIELD OF THE INVENTION

The present invention relates to a method for improving the effectiveness of immunotherapies and/or for improving the effectiveness of combination therapies of medicinal product treatments with immunotherapies. Immunotherapies are used in particular in the treatment of cancer, but also in the treatment of autoimmune diseases, in the support of transplants and in vaccination against viruses.

BACKGROUND OF THE INVENTION

Besides the conventional treatment of cancer, which is based on surgical measures, the use of chemotherapy medicaments and/or irradiation, immunotherapy with antibodies has become established. Equally, a large number of biotechnological products which also include, inter alia, therapeutic antibodies, are already recognized as a therapy option for the treatment of autoimmune diseases. So-called HIV-neutralizing antibodies are currently being investigated for the treatment of AIDS in clinical studies.

The target structures, the so-called antigens, differ greatly for the various diseases and thus the mode of action of the respective antibody therapies can be very different depending on these target structures. Surface antigens which serve as target structure for the treatment of malignant diseases, include inter alia overexpressed, cancer-associated, membrane-bound proteins (EGFR/HER2/VEGFR) or also cell-specific proteins (CD20/CD52). The number of antigen-positive cells in the development of lymphomas is extremely large, with the result that a reduction in this cell population represents a recognized therapeutic aim. Besides the treatment of lymphomas the target-oriented depletion of antigen-positive cells is also suitable for the treatment of autoimmune diseases and optionally for the suppression of the immune response such as e.g. in the case of transplantation. Antibodies or also fusion proteins, directed against cellular messengers such as the soluble tumour necrosis factor, are important medicaments for the treatment of autoimmune diseases.

The first modern monoclonal antibodies (immunoglobulins mostly of the IgG1 type) were of murine origin, i.e. they were prepared by means of mouse or rat hybridoma cell lines. These IgG1 molecules are however recognized as foreign by the human body, with the result that they are neutralized by the human immune system. For this reason, more modern, so-called chimeric antibodies have been prepared, consisting of murine portions and human portions in the IgG structure. So-called "humanization", up to the biotechnologically optimized variant of the completely human antibodies, represents the next step towards the further minimization of the murine portions. Chimeric, humanized and human IgG1 antibodies can be used over a longer period, for example over months, during therapy. (Abdullah N., Cancer Immunther. 48, 517-524), (Adams G P, Weiner L M, Nature Biotechnology, 2005; 23 (9): 1146-1157).

Moreover, immunotherapies are carried out inter alia with Fcγ receptor-binding agents. Fcγ receptors (FCRs) are a family of receptors which are specific to the Fc parts of immunoglobulin (IgG). These receptors have important tasks in the normal immune system and its resistance to infections. Thus IgGs are a class of molecules which bind the Fcγ receptor.

There are receptors for each immunoglobulin class. They are defined by the class of immunoglobulin to which they bind. For example the Fcγ receptor (FcγR) binds IgG, the Fcε receptor (FcεR) binds IgE etc. Among the FcγR receptors a distinction is made between three members of sub-families: FcγRI, which is a receptor with high affinity for IgG, FcγRIIs, which are receptors with low affinity for IgG, but which bind well to aggregates of immune complexes, and FcγRIIIs, which are receptors with low affinity which bind to immune complexes.

Although all these receptors are structurally related to each other, they have different tasks.

SUMMARY OF INVENTION

The present invention provides an ex-vivo method for increasing the effectiveness of antibodies and Fcγ receptor-binding active ingredients, comprising the steps of preparing a blood sample of a patient, subjecting the blood sample to an immunoapheresis and administering a therapeutically effective antibody or an Fcγ receptor-binding active ingredient to a patient.

BRIEF DESCRIPTION OF DRAWINGS

FIG. 1 illustrates a plot of Herceptin (mg/mL) against the survival rate relative to the untreated control sample.

DETAILED DESCRIPTION OF THE INVENTION

FCγRs are expressed by most haematopoietic cells and, via the binding to IgG, play a key role in the homeostasis of the immune system and protection against infections. In particular FcγRII is a receptor with low affinity for IgG, which essentially binds only to IgG-immune complexes, and it is expressed on a large number of cell pieces, including for example monocytes, macrophages, neutrophils, eosinophils, platelets and B-lymphocytes.

Fcγ receptors are involved in various immune and inflammatory responses including antibody-dependent cell-mediated cytotoxicity (ADCC). Antibody-dependent cell-mediated cytotoxicity (ADCC) is responsible for the effect of biological medicinal products such as e.g. poly- and monoclonal antibodies, but also of fusion proteins. The effectiveness of the ADCC is directly related to the described interaction of the constant region of the antibody, or also to the binding properties of the corresponding protein with the Fcγ receptors. For the ADCC, the binding seems to be above all to the activating Fcγ I and III receptors; whereas the binding of a medicinal product predominantly to FcγII receptors suppresses the immune response.

A continuous use of therapeutic proteins, such as e.g. of antibodies, or of FcR-binding agents, in particular for the treatment of cancer and autoimmune diseases, infectious diseases and for the suppression of transplant rejection reactions, is limited by the fact that these medicaments have to be used in high doses during a continuous therapy.

When using antibodies of another, but even also humanized or human antibodies, these foreign proteins are recognized by the patient's immune system and depending on the respective immunogenicity neutralized by the development of the body's own (autologous) antibodies (human anti-species antibodies). This immune response is mediated by e.g.

human anti-murine antibodies (HAMA) in the case of murine antibodies, HARA in the case of antibodies from rabbits, (HAMA) in the case of murine antibodies or by human anti-human antibodies (HAHA) in the case of humanized or human antibodies. Naturally, mono- and polyclonal antibody products which are obtained from other species such as e.g. rats, horses, goats, sheep, cattle or also pigs, also induce the development of human antibodies directed against the respective species, which can often lead to strong immune reactions and to a loss of effectiveness. This form of the autologous antibodies against antibodies from other organisms is collectively known as human anti-species antibodies.

The immunogenicity of the exogenous, biotechnological products limits their therapeutic effectiveness e.g. by the development of the HAMA and HAHA response, described above, of the immune system.

The relatively low effectiveness observed in vivo of therapeutic antibody preparations contrasts strongly with the often very high antibody-mediated cellular cytotoxicity (ADCC) which had been detected in previous in vitro investigations. This phenomenon also occurs in combination therapies of conventional medicinal product treatments, e.g. chemotherapies, with immunotherapies. If medicinal products are generally mentioned hereafter, conventional medicinal products without immunotherapeutic effect are meant, quite particularly including chemotherapeutics and/or cytostatics. A possible explanation for this phenomenon is the described inhibition of the therapeutic antibodies by HAMA/HAHA (Preithner, S. et al. in Molecular Immunology, 43 (2006) 1183-1193.) Furthermore, the naturally occurring IgG1s in the patient's blood represent molecules which compete comparably with the therapeutic antibodies for the corresponding Fc receptors, as these IgG1s also bind to the corresponding receptors and thereby occupy these.

It was expected that humanized or human antibodies would lead to an improved effectiveness and to a better safety profile. As already mentioned above, almost all humanized or human antibodies surprisingly also exhibit a dramatically reduced effectiveness in vivo, compared with their in vitro activity.

It is therefore necessary to administer to the patient doses of antibodies which are several times higher, whereby the risk of undesired side effects is increased.

In the case of a targeted use of standard chemotherapies in combination with antibody-based immunotherapies which are an accepted standard therapy in the field of oncology for the treatment of various malignant diseases, such as e.g. in the case of breast cancer (trastuzumab), lymphomas (rituximab) or also in the case of bowel cancer (cetuximab and panitumumab), the necessary effectiveness is also not achieved in vivo, as already indicated above.

The synergistic increase in effectiveness of the combination therapy has been described clinically and pre-clinically. More recent findings based on in vitro experiments prove that the interaction with the FcR-positive cells, such as e.g. NK, DC and the like, form the basis of the observed synergism. It has been demonstrated that, on the one hand through the use of medicinal products, such as e.g. paclitaxel (Miura D. et al., Journal of Clinical Oncology, 2007, Part I. Vol 25, No. 18S (June 20 Supplement), lenalidomide and pomalidomide (Bartlett J. B. et al., Journal of Clinical Oncology, 2007 ASCO Annual Meeting Proceedings Part I. Vol 25, No. 18S (June 20 Supplement)), but also kinase inhibitors, such as e.g. sorafinib (Hipp et al, Journal of Clinical Oncology, 2007 ASCO Annual Meeting Proceedings Part I. Vol 25, No. 18S (June 20 Supplement) have a direct influence on the homeostasis of the antigen-presenting cells but also on various T-cell populations, such as e.g. cytotoxic T-lymphocytes (CTLs). For sorafinib, a negative influence on antigen-presenting cells and the development of a CTL response have been demonstrated, which is why kinase inhibitors such as sunitib appear to be suitable for a combination therapy with immunotherapeutics, as do various Her2 kinase inhibitors such as e.g. lapatinib or also canertinib. In the works cited above, the synergistic effect was ascribed to the FcR-positive cell populations which mediate the ADCC.

Clinically, in the case of the existing combination therapies it is unfortunately to be noted that a majority of the patients treated develop resistance mechanisms to the chemotherapy used and to the corresponding antibody-based immunotherapy. Various mechanisms play a role in this, independently of each other. Some target-dependent but also target-independent resistance mechanisms have been described for the immunotherapies listed above (Herceptin: Ritter CA. et al., Clinical Cancer Research 2007, 13 (16): 4909-4919; Valabrega G. et al., Annals of Oncology, 2007; Nahta R, et al., Natl Clin Pract Oncol 2006, 3:269-280; Esteva F J et al., J Clin Oncol 2002, 20:1800-1808; Nagata Y et al., Cancer Cell 2004, 6:117-127; Scaltriti M et al., J Natl Cancer Inst 2007, 99:628-638; Rituximab: Van Meerten T et al., Clinical Cancer Research Vol. 12, 4027-4035, Jul. 1, 2006).

R. A. Montgomery et al. describes (Transplantation, Vol. 70, 887-895, Sep. 27, 2000) a therapeutic procedure for preventing organ transplant rejection reactions. In this, a plasmapheresis (PP) is combined with intravenous gamma globulin (IVIG) and cytogam. An overdose of administered Ig antibodies in the blood of the patient leads to a blockade of Fc receptors and thus to an immunosuppression. However, a blockade of the Fc receptors is not desired within the meaning of the invention, but on the contrary, the Fc receptors are specifically to be kept free of antibodies, in order that therapeutic antibodies can bind to these sites and effect an ADCC. A combination of PP/IVIG and optionally cytogam is therefore to be ruled out.

H. Borberg discloses a method for reducing IgG by means of an anti-IgG adsorption column (H. Borberg, Transfusion and Apheresis Science, 34, 2006, 51-73) in combination with an IVIG administration. The above-described problems of a blocking of the Fc receptors are also the consequence here.

U.S. Pat. No. 6,406,861 B1 discloses a method for reducing virus antibodies, in particular adenovirus antibodies, by extracorporeal adsorption with the aim of improving the efficiency of a viral vector therapy. U.S. Pat. No. 6,406,861 B1 does not therefore relate to an immune therapy.

The object of the present invention was therefore in particular to improve the effectiveness of Fcγ-R-binding agents, in particular antibodies, with the result that the disadvantages described above can be avoided.

A further object was to reduce the resistance formation resulting within the framework of combination therapies of conventional medicinal product treatments with immunotherapies, in particular to increase the efficiency of such combination therapies.

According to the invention the object is achieved by an ex-vivo method for increasing the effectiveness of antibodies and Fcγ receptor-binding active ingredients, comprising the steps of a) preparing a blood sample of a patient;
b) subjecting the blood sample to an immunoapheresis;
c) administering a therapeutically effective antibody or an Fcγ receptor-binding active ingredient to the patient.

and before or after step c) optionally administering the thus-treated blood sample to a patient.

A medicinal product can be administered as an additional step d). A combination therapy is thereby obtained, consisting of a medicinal product treatment with an immunotherapy.

A subject of the present invention is also the use of Fcγ receptor-binding active ingredients to prepare a medicament for the treatment of cancer and/or autoimmune diseases and/or patients who have had a transplant and/or for vaccination against viruses, wherein the treatment comprises the steps of:
  a) preparing a blood sample of a patient;
  b) subjecting the blood sample to an immunoapheresis;
  c) administering the medicament to the patient,
and before or after step c) optionally administering the thus-treated blood sample to a patient.

The Fcγ receptor-binding active ingredient within the framework of the invention is preferably a therapeutic antibody, particularly preferably a monoclonal and/or recombinant antibody or an active ingredient with FcR-binding regions, consisting of antibody fragments or peptides bound to a therapeutic agent.

A medicinal product can be administered as an additional step d). A combination therapy is thus obtained, consisting of a medicinal product treatment with an immunotherapy.

A combination therapy consisting of medicinal products or their combinations, which together with FcR-binding immunoglobulins, their fragments or also fusion proteins have an ADCC-mediated effectiveness, and which has clear synergies in the antitumour effect, can therefore be seen as a subject of the invention.

A subject of the invention is therefore also the use of a combination of one or more medicinal products together with FcR-binding immunoglobulins, fragments of immunoglobulins or fusion proteins, to prepare a medicament for the treatment of cancer and/or autoimmune diseases and/or of patients who have had a transplant and/or for vaccination against viruses, wherein the treatment comprises the steps of:
  a) preparing a blood sample of a patient;
  b) subjecting the blood sample to an immunoapheresis;
  c) administering the medicament to the patient,
and before or after step c) optionally administering the thus-treated blood sample to a patient.

FcR- or Fcγ-binding active ingredients within the meaning of this invention are active ingredients with a binding affinity with a Kd value of less than 1 mM.

The combination therapy is preferably to take place with immunoglobulins, their fragments or also fusion proteins, which bind CD16 or CD64 in targeted manner.

It is further preferred that the immunoglobulins, their fragments or fusion proteins induce a T-cell-mediated immune response in addition to the ADCC.

It is yet further preferred that the immunoglobulins, their fragments or fusion proteins contain bispecific antibodies with a CD3 binding arm.

Also preferred is a combination therapy with immunoglobulins, their fragments or also fusion proteins, in which the occurrence of resistances is avoided by the previously named antitumour cell responses.

Preferred medicinal products for the method according to the invention or the use according to the invention are cytostatics and chemotherapeutics, in particular paclitaxel, lenalidomide, pomalidomide, epirubicin, 5FU and its derivatives, and kinase inhibitors such as sunitinib, lapatinib, canertinib. Furthermore, combinations of various medicinal products such as CHOP, cyclophosphamides, doxorubicin, vincristine, prednisolone (steroid), lenalidomide/dexamethasone, pomalidomide/dexamethasone and paclitaxel/carboplatin can also be used.

With the methods or uses according to the invention immunoglobulins with human, chimeric, murine, and hybrid immunoglobulins, their fragments or also fusion proteins which possess CD16/CD64 binding properties can be used. Further preferred are immunoglobulins which are tumour-associated antigens, antigens which are associated with lymphomas or leukaemia, as well as antigens which are associated with autoimmune diseases. These are Her2/neu, EGFR, Epcam, VEGF, VEGFR, MUC-I, CA 125, CEA, MAGE, CD20, CD19, CD40, CD33, carbonic anhydrase IX, A3, antigen specific to A33 antibodies, BrE3 antigen, CD1, CDIa, CD4, CD5, CD8, CD14, CD15, CD16, CD21, CD22, CD23, CD25, CD30, CD37, CD38, CD40, CD40L CD45, CD46, CD52, CD54, CD74, CD79a, CD80, CD126, CD138, CD154, B7, Ia, Ii, HM1.24, HLA-DR, NCA95, NCA90, HCG and sub-units, CEA (CEACAM5), CEACAM-6, CSAp, EGFR, EGP-I, EGP-2, Ba 733, hypoxia-inducing factor (HIF), KC4 antigen, KS-I antigen, KS1-4, Le-Y, macrophage-inhibiting factor (MIF), MUC2, MUC3, MUC4, PlGF, ED-B fibronectin, NCA 66a-d, PAM-4 antigen, PSA, PSMA, RS5, SlOO, TAG-72, TIOl, TAG TRAIL-Rl, TRAIL-R2, p53, tenascin, IL-[beta], IL-8, insulin growth factor-1 (IGF-I), Tn antigen, Thomson-Friedenreich antigens, tumour necrosis antigens and analogues thereof and bind FcR-positive cells.

A subject of the invention is also a combination therapy comprising immunotherapies and immunologically active methods which directly influence FcR-positive cells, wherein the method lowers the immunoglobulin concentration in the blood. It is particularly preferred if the method which lowers the immunoglobulin concentration is an extracorporeal method. It is further preferred if the method is an adsorption method which binds the naturally occurring immunoglobulins and immunoglobulin complexes. The method is additionally to exhibit a synergism between the medicinal products used, their combinations and the immunotherapies.

In the respective step b) of the abovementioned methods or uses, autologous antibodies or Fcγ-R-binding agents are removed from the blood sample by the immunoapheresis.

The surprising result of removing human anti-species antibodies and IgG antibodies from the patient before the administration of the therapeutic antibody and in the case of a combination therapy also before the administration of the medicinal product is that the effectiveness of the antibody therapy and also of the combination therapy can be increased several fold, and the effectiveness in vivo now virtually corresponds to the expected effectiveness as determined in vitro. The dosing of therapeutic antibodies can be reduced at least 5-fold, preferably 10-fold and in quite particularly preferred embodiments 20-fold, compared with the dosing of therapeutic antibodies in conventional methods.

The combination of medicinal products with immunotherapies which, in addition to the tumour-associated antigen, bind FcR-positive cells in targeted manner, thereby overcome possible resistance developments which could be mediated by the antigens (Her2/EGFR/CD20), secondary intracellular signal transduction cascades (apoptosis or PTEN loss), or other kinase activities (HER3/PI3K/Akt). These immunotherapies recruit antigen-presenting cells in targeted manner, whereby T-cells are in turn activated via co-stimulatory (CD28/CD40) signals.

Ideal candidates for a combination therapy are humanized complete and IgG-like bispecific antibodies (Asano et al., 2007, JBC) and trifunctional bispecific antibodies, preferably mouse/rat IgG2a/IgG2b chimeras. In the case of these mouse/rat IgG2a/IgG2b chimeras T-cells are even still bound in targeted manner to the FcR I and III-positive cells by the second CD-3-binding arm. Both receptors are among the ADCC-mediating receptors.

In addition to the trifunctional antibodies, various other immunotherapies already exist which recruit CD16 or also CD64 positive cells (Her2/CD16; CD30/CD16; CD19/CD64; CD15/CD64; Her2/CD64 etc.) in targeted manner or intensify the ADCC by improved FcR binding properties. Such immunotherapies are also suitable candidates for combination therapy in which potential resistance mechanisms can be circumvented and a synergistic therapy can be conceived.

The already described synergistic effects of a combination therapy consisting of the above-named medicinal products and immunotherapy can be still further intensified with the immunoadsorption method described above. The targeted depletion of the naturally occurring immunoglobulins by extracorporeal immunoadsorption is to take place in this case before the combination therapy. In the process, the ADCC would be still further intensified, as the concentration of the immunoglobulins is reduced and thus more FcRs are available in an unbound state on the cell surfaces. The synergistic influence of the immunoadsorption process can be exploited for use with medicinal products as mono and/or combination therapies. As an example of this, sunitinib or also paclitaxel/carboplatin or lenalidomide/dexamethasone may be cited.

The medicinal product/immunotherapy combinations can be further strengthened with this method. However, a particularly strong synergism results from interaction with the combination therapy consisting of medicinal products with FcR-directed immunotherapies.

A combination therapy with humanized and IgG-like bispecific antibodies and/or trifunctional antibodies and an upstream immunoadsorption not only brings about a stronger synergy as regards the ADCC and T-cell-mediated cytotoxicity, but also makes possible the long-term treatment of the combination therapy with the murine antibodies. The upstream immunoadsorption also neutralizes the potentially neutralizing immunoglobulins (HAMA, ADA) which are themselves directed against the therapeutic antibodies.

As a result of the removal of the autologous antibodies, the immune reaction to the therapeutic antibodies turns out to be much milder and the effectiveness of the therapeutic antibodies is thereby surprisingly intensified in vivo.

Molecules interacting with Fcγ receptors are e.g. immunoglobulins or also the pro-inflammatory C-reactive protein (Das, T., FEBS Lett., 2004) which occupy the available Fcγ receptors.

An example according to the invention is antibody-mediated cellular cytotoxicity (ADCC) which is responsible for the effect of biological medicinal products, such as e.g. poly- and monoclonal antibodies, but also of fusion proteins. The effectiveness of the ADCC is directly related to the interaction of the constant region of the antibody but also to the binding properties of the corresponding protein with the Fcγ receptors. The binding to the activating FcγI and III receptors seems to be especially relevant for the ADCC in this connection. The binding of a medicinal product predominantly to FcγII receptors on the other hand suppresses the immune response. For example there are bi-specific antibodies which are directed against a target protein such as e.g. HER2 but also at the same time against the Fcγ receptor I or the Fcγ receptor III.

Further preferred active ingredients which bind Fcγ receptors are typically polyclonal and monoclonal antibodies of animal and human origin, recombinant antibodies, chimeric, primatized, humanized and human monoclonal antibodies, antibody domains and fragments thereof, bi-, tri- and multi-specific antibodies and constructs of antibody fragments as well as molecules or active ingredients which can specifically bind Fcγ receptors, such as natural and recombinant proteins and peptides which interact with the Fcγ receptor, fusion proteins which interact with Fcγ receptors, synthetic peptides which interact with Fcγ receptors and soluble Fcγ receptors. By this is also meant treatments with active ingredients which influence the expression of Fcγ receptors, such as treatments with cytokines and cytokine fusion proteins, hormones or derivatives, steroids, glucocorticoids and dopaminergic substances.

For example the development of inoculation strategies exploiting the targeted control of Fcγ receptor-positive dendritic cells, e.g. by the coupling of DNA vaccines to IgG structures (Zhaoyang You et al., 2001, Cancer Research) illustrates the range of possible uses which are opened up by Fc receptors and agents binding to them.

As a result of removing the molecules interacting with Fcγ receptors in the blood, there is less competition for the binding sites for a subsequently administered Fcγ-R-binding active ingredient, so that the Fcγ-R-binding active ingredients can now bind preferentially.

After the treatment with therapeutic antibodies or with Fcγ receptor-binding active ingredients, or after the combination therapy, in preferred embodiments of the method according to the invention the autologous antibodies can for example also be returned to the patient following the administration of the Fc-R-binding agents.

The method can be carried out both continuously, i.e. extracorporeally in a cycle, and also discontinuously, after which in each case blood is taken from the patient, subjected to the method according to the invention and subsequently returned to the patient.

The temporary removal of human anti-species antibodies, such as e.g. HAMA and HARA and of IgG antibodies in general is safe for the patient and does not increase the risk of infections.

Step b) of the method according to the invention is carried out several times in preferred developments. Up to 80%, preferably 90%, and still more preferably up to 95% of the corresponding antibodies or Fcγ receptor-binding active ingredients can be removed from the blood of the patient.

According to the invention the blood sample can be human blood or blood plasma. The plasma can be obtained in an upstream stage e.g. by plasma filtration or cell separation by centrifugation of the blood.

Thus for example the blood of the patient or the plasma can also be passed in an extracorporeal step over an adsorber which binds Fcγ-binding agents, in particular antibodies. The blood or plasma can then be returned to the patient.

The object of the present invention is further achieved by the use of specific ligands for autologous antibodies with Fcγ receptor-binding regions to prepare a column which has the specific ligand coupled to it, for the treatment of a patient with Fcγ receptor-binding active ingredients, wherein the treatment comprises the steps of:

a) preparing a blood sample of a patient;
b) subjecting the blood sample to an immunoapheresis;
c) administering an Fcγ receptor-binding active ingredient to the patient and before or after step c) optionally administering the thus-treated blood sample to a patient.

By the term "specific ligands" is meant ligands which selectively remove antibodies from the blood, but not other components of the blood.

As a specific ligand it is possible to use for example protein A, or molecules which are equivalent to Fcγ receptors in their effect, fragments thereof, synthetic peptides, proteins, etc. Further examples are given below.

The object of the present invention is further achieved by the use of specific ligands for autologous antibodies to prepare a column which has the ligand coupled to it for the treatment of a patient with therapeutic antibodies, wherein the treatment comprises the steps of:
 a) preparing a blood sample of a patient;
 b) subjecting the blood sample to an immunoapheresis;
 c) administering an Fcγ receptor-binding active ingredient to the patient.
and before or after step c) optionally administering the thus-treated blood sample to a patient.

The matrix of the column used according to the invention for the immunoapheresis consists of sepharose or acrylic compounds, as described e.g. in EP 222 146 B1.

Before the application of the ligand the matrix is preferably activated with CN—Br or compounds with similar effect.

Protein A, protein G, peptides or anti-antibodies are preferably used as ligands. FcR receptors, fragments thereof, or equivalent natural or synthetic molecules with equivalent binding properties also come into consideration as ligands.

In further preferred embodiments of the invention the extracorporeal removal of human anti-species antibodies and IgG antibodies is achieved by a combination system which consists of a device for the production of blood plasma and a second device in which the plasma is passed over an adsorber column. This adsorber column operates in principle as a chromatography column.

The adsorber column typically consists of a biocompatible plastic casing and contains 20 to 1500 ml of an inert matrix on which specific ligands with an affinity for example for human anti-species antibodies such as HAMA, HARA and human IgG1 are immobilized.

If the plasma is passed over the adsorber column, the human anti-species antibodies and IgG1 antibodies from the patient's blood are bound by these ligands and therefore eliminated from the plasma.

Such systems or materials are for example known from EP 0 082 345.

The adsorber columns can are regenerable and can be used repeatedly.

In a typical two-column system only one column is in use, while the second column is automatically regenerated. In this way the speed for the reduction of the species to be depleted can be increased by up to 60% during a single treatment session.

Alternatively larger columns with more selective ligands and a higher adsorption capacity can also be used as single columns.

The object of the present invention is further achieved by the use of specific ligands for cancer-associated antigens (cancer markers), wherein the cancer marker is soluble in the blood, to prepare a column which has the specific ligand coupled to it, for the treatment of a patient with tumour-specific antibodies, wherein the treatment comprises the steps of:
 a) preparing a blood sample of a patient;
 b) subjecting the blood sample to an apheresis, removing the cancer-associated antigens;
 c) administering a therapeutically effective antibody to the patient.
and before or after step c) optionally administering the thus-treated blood sample to a patient.

Antibody-based therapies which are themselves directed against soluble and cell membrane-bound cancer-associated antigens are currently undergoing clinical evaluation. Such cancer-associated antigens include inter alia CH125, PSA, MUC1, MAGE-I, HER2, CEA, AFP, EpCAM. The specific ligand used possesses a high specific binding affinity to the cancer-associated antigen. In particular specific antibodies against cancer-associated antigens can be used as ligands.

A specific adsorption according to the invention of the soluble cancer-associated antigens leads to the therapeutic antibodies or also peptides being prevented from complexing with freely soluble antigens. In this way the active ingredient concentration at the target structure, the antigen on the cell, is increased and effectiveness thus increased. Furthermore, the antibody-mediated cellular cytotoxicity (ADCC) can thus be made possible as the primary immune response, directed against the antigen-positive tumour and therefore extremely efficient. Furthermore the specific adsorption, for example of PSA, leads to an increase in the effectiveness of soluble T-cell receptors which specifically bind to PSA.

The invention is further explained using a non-limiting example with reference to FIG. 1.

EXAMPLE 1

Elimination of the Serum Inhibition of Herceptin-Mediated ADCC by IgG Adsorption Experimental Structure:
 1. Sowing of tumour cells (Her-2/neu positive SK-OV-3 ovary cells) overnight;
 2. Isolation of PBMC (peripheral mononuclear blood cells) from the buffy coat (leukocyte film);
 3. Co-culturing of PBMC and tumour cells with herceptin in the presence of IgG-depleted (Sa) and native serum (Sn);
 4. The herceptin concentrations are 0.0001, 0.001, 0.01, 0.1, 1 and 10 µg/ml;
 5. The incubation period was 20 hours;
 6. The cytotoxicity was measured by means of XTT;

FIG. 1 shows that the cytotoxicity of the PBMC is eliminated by adding normal, human serum (PBMC+Sn curve). After adding IgG-depleted plasma (PBMC+Sa curve) the cytotoxicity of the PBMC remains. In the lower range of the herceptin concentration it is further increased.

The invention claimed is:
1. A method for increasing the effectiveness of a therapeutically effective antibody or an FCγ receptor binding active ingredient, comprising
 a) subjecting a patient's blood to an immunoapheresis, which removes 80% or more of native antibodies or FCγ receptor binding active ingredients from the blood;
 b) re-administering the blood subjected to said immunoaphersis to said patient; and
 c) administering a therapeutically effective antibody or an Fcγ receptor-binding active ingredient to said patient; wherein the blood subjected to immunoapheresis is administered before said administration of said therapeutically effective antibody or said FCγ receptor-binding active ingredient.
2. The method according to claim 1, wherein said immunoapheresis removes antibodies from the blood.
3. The method according to claim 2, further comprising
 (d) re-administering the removed native antibodies or native FCγ receptor binding active ingredients to the patient after said administration of said therapeutically effective antibody or said FCγ receptor-binding active ingredient.

4. The method according to claim 2, wherein the removed antibodies are human anti-species antibodies.

5. The method according to claim 2, wherein the removed antibodies are autologous antibodies with Fcγ receptor-binding epitopes.

6. The method according to claim 1, wherein said immunoapheresis is carried out several times.

7. The method according to claim 1, wherein the blood is human blood or blood plasma.

8. The method according to claim 1, further comprising administering a medicinal product.

9. The method according to claim 8, wherein the medicinal product is a chemotherapeutic agent or a cytostatic agent.

10. The method according to claim 8, wherein the medicinal product is
 paclitaxel, lenalidomide, pomalidomide, epirubicin, 5FU or a derivative thereof,
 a kinase inhibitor which is sunitinib, lapatinib, or canertinib, or
 a combination comprising cyclophosphamide, hydroxydaunorubicin, oncovin and prednisone (CHOP),
 a combination comprising lenalidomide and dexamethasone,
 a combination comprising pomalidomide and dexamethasone, or
 a combination comprising paclitaxel and carboplatin.

11. The method according to claim 1, wherein the therapeutically effective antibody is a bispecific antibody.

12. The method according to claim 11, wherein the therapeutically effective antibody is a bispecific trifunctional antibody.

13. The method according to claim 12, wherein the bispecific trifunctional antibody is a mouse/rat/IgG2a/IgG2b chimera.

14. The method according to claim 1, wherein said immunoapheresis removes antibodies which are human anti-species antibodies.

15. The method according to claim 1, wherein said immunoapheresis removes antibodies which are
 (a) human anti-murine antibodies (HAMA) in the case of murine antibodies,
 (b) human anti-rabbit antibodies (HARA) in the case of antibodies from rabbits,
 (c) human anti-human antibodies (HAHA) in the case of humanized or human antibodies; or
 (d) immunoglobulin G (IgG) antibodies.

16. The method according to claim 1, wherein the Fcγ receptor binding active ingredient is an immunoglobulin G (IgG) molecule.

17. The method according to claim 1, wherein the Fcγ receptor binding active ingredient is an immunoglobulin G 1 (IgG1) molecule.

* * * * *